(12) United States Patent
Kobayashi

(10) Patent No.: US 12,171,402 B2
(45) Date of Patent: Dec. 24, 2024

(54) ENDOSCOPE HAVING A RELAY

(71) Applicant: HOYA CORPORATION, Tokyo (JP)

(72) Inventor: Takahiro Kobayashi, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 430 days.

(21) Appl. No.: 17/637,217

(22) PCT Filed: Aug. 24, 2020

(86) PCT No.: PCT/JP2020/031772
§ 371 (c)(1),
(2) Date: Feb. 22, 2022

(87) PCT Pub. No.: WO2021/039690
PCT Pub. Date: Mar. 4, 2021

(65) Prior Publication Data
US 2022/0296084 A1    Sep. 22, 2022

(30) Foreign Application Priority Data
Aug. 28, 2019 (JP) ................. 2019-155965

(51) Int. Cl.
*A61B 1/012* (2006.01)
*A61B 1/00* (2006.01)
*A61B 1/015* (2006.01)

(52) U.S. Cl.
CPC ...... *A61B 1/00133* (2013.01); *A61B 1/00071* (2013.01); *A61B 1/00119* (2013.01);
(Continued)

(58) Field of Classification Search
CPC .................................................... A61B 1/015
(Continued)

(56) References Cited

U.S. PATENT DOCUMENTS 4,270,525 A * 6/1981 Furihata ............... A61M 1/76
600/154
5,201,908 A * 4/1993 Jones ...................... A61B 1/12
600/125
(Continued)

FOREIGN PATENT DOCUMENTS

JP    H04-259439 A    9/1992
JP    11-253393       9/1999
(Continued)

OTHER PUBLICATIONS

Extended European Search Report issued in related EP application No. 20858655.2, dated Aug. 1, 2023.
(Continued)

*Primary Examiner* — John P Leubecker
(74) *Attorney, Agent, or Firm* — GREENBLUM & BERNSTEIN, P.L.C.

(57) ABSTRACT

Provided is an endoscope that allows improving assembly workability to assemble various types of conduits inside an insertion portion and facilitating maintenance. The endoscope includes an insertion portion, a hand operating unit coupled to the insertion portion, a plurality of conduits disposed inside the insertion portion and the hand operating unit, a base plate as a fixing member fixedly disposed to the hand operating unit, and a relay portion (a first relay portion and a second relay portion) that relays the plurality of conduits. The relay portion has a structure fixable to the base plate.

3 Claims, 8 Drawing Sheets

(52) U.S. Cl.
CPC .......... *A61B 1/00128* (2013.01); *A61B 1/012* (2013.01); *A61B 1/015* (2013.01)

(58) Field of Classification Search
USPC .................................................. 600/136, 159
See application file for complete search history.

(56) References Cited

U.S. PATENT DOCUMENTS

| | | | | |
|---|---|---|---|---|
| 5,447,148 | A * | 9/1995 | Oneda | A61B 1/00142 |
| | | | | 600/131 |
| 6,334,844 | B1 * | 1/2002 | Akiba | A61B 1/00068 |
| | | | | 600/156 |
| 6,383,132 | B1 * | 5/2002 | Wimmer | A61B 1/12 |
| | | | | 600/101 |
| 6,569,087 | B2 | 5/2003 | Naito et al. | |
| 2001/0025135 | A1 | 9/2001 | Naito et al. | |
| 2003/0122374 | A1 * | 7/2003 | Ouchi | A61B 1/00128 |
| | | | | 285/120.1 |
| 2007/0043262 | A1 * | 2/2007 | Levy | A61B 1/015 |
| | | | | 600/156 |
| 2007/0060789 | A1 * | 3/2007 | Uchimura | A61B 1/00105 |
| | | | | 600/110 |
| 2007/0238927 | A1 * | 10/2007 | Ueno | A61B 1/00105 |
| | | | | 600/152 |
| 2009/0281388 | A1 | 11/2009 | Ito | |
| 2014/0107416 | A1 * | 4/2014 | Birnkrant | A61B 1/00124 |
| | | | | 600/110 |
| 2015/0011831 | A1 * | 1/2015 | Ouchi | A61B 1/05 |
| | | | | 600/159 |

FOREIGN PATENT DOCUMENTS

| | | |
|---|---|---|
| JP | 2003-033320 | 2/2003 |
| JP | 3488170 | 1/2004 |
| JP | 2007-185387 A | 7/2007 |
| JP | 2008-272299 | 11/2008 |
| JP | 2009-142562 | 7/2009 |

OTHER PUBLICATIONS

International Search Report issued in International Bureau of WIPO Patent Application No. PCT/JP2020/031772, dated Oct. 13, 2020.
Written Opinion issued in International Bureau of WIPO Patent Application No. PCT/JP2020/031772, dated Oct. 13, 2020, along with an English translation thereof.

* cited by examiner

ENDOSCOPE HAVING A RELAY

TECHNICAL FIELD

The present invention relates to an endoscope.

BACKGROUND ART

An endoscope apparatus generally includes an insertion portion to be inserted into an inside of a body (for example, a digestive organ) of a subject. The insertion portion includes a light guide to transmit light and an electrical wiring to transmit electrical signal from an imaging unit disposed at a distal end portion.

In addition to them, the insertion portion internally includes various types of conduits including, for example, an air supply/water supply conduit to supply air and supply water, a suction conduit to suction a bodily fluid and a resected substance from the inside of the body, and a treatment instrument conduit to insert and remove a treatment instrument. An endoscope is required to couple these conduits without causing a poor connection or the like. Additionally, ease of the assembly has been desired from aspects of cost reduction and ease of maintenance.

As a technique that allows the ease of coupling of the various types of conduits to improve assembly workability, and to improve the ease of maintenance, for example, there has been known an endoscope described in Patent Literature 1. In this endoscope, a water supply/air supply conduit is dividable, and at the divided position, the front and rear conduits are relayed (coupled) with a relay member. According to the apparatus of this Patent Literature 1, pipework and replacement of various types of conduits are facilitated, thereby ensuring cost reduction and ease of maintenance.

However, although the apparatus in Patent Literature 1 allows the division of the conduit, there is a problem of insufficient working efficiency. Moreover, since the large number of types of conduits are present inside an insertion portion, it was not easy to reliably couple the same type of conduits without any connection error.

CITATION LIST

Patent Literature

Patent Literature 1: Japanese Patent No. 3488170

SUMMARY OF INVENTION

Technical Problem

The present invention has been made in consideration of the above-described problems, and an object of the present invention is to provide an endoscope that allows improving assembly workability to assemble various types of conduits inside the endoscope and facilitating maintenance.

Solution to Problem

In order to solve the problems, an endoscope according to the present invention comprises: an insertion portion; a hand operating unit coupled to the insertion portion; a plurality of conduits disposed inside the insertion portion and the hand operating unit; a fixing member fixedly disposed to the hand operating unit; and a relay portion that relays the plurality of conduits. The relay portion has a structure fixable to the fixing member.

Advantageous Effects of Invention

The endoscope according to the present invention allows improving assembly workability to assemble various types of the conduits inside the insertion portion and facilitating maintenance.

DESCRIPTION OF EMBODIMENTS

In the following, the present embodiments will be described with reference to the attached drawings. In the attached drawings, functionally identical elements may be designated with identical numerals. While the attached drawings illustrate embodiments and implementation examples in accordance with the principle of the present disclosure, the embodiments and implementation examples are provided to aid in understanding the present disclosure and should not be interpreted as limiting the present disclosure. The descriptions provided herein are merely illustrations of typical examples and are not intended as limiting in anyway the scope of the claims of the present disclosure or application examples thereof.

The embodiments will be described in such sufficient detail as to enable those skilled in the art to carry out the present disclosure. However, it should be understood that other implementations and modes are also possible, and that various modifications of configurations and structures and substitutions of various elements are possible without departing from the scope and spirit of the technical concepts of the present disclosure. Accordingly, the following descriptions are not to be regarded as limiting.

First Embodiment

Figure 1:
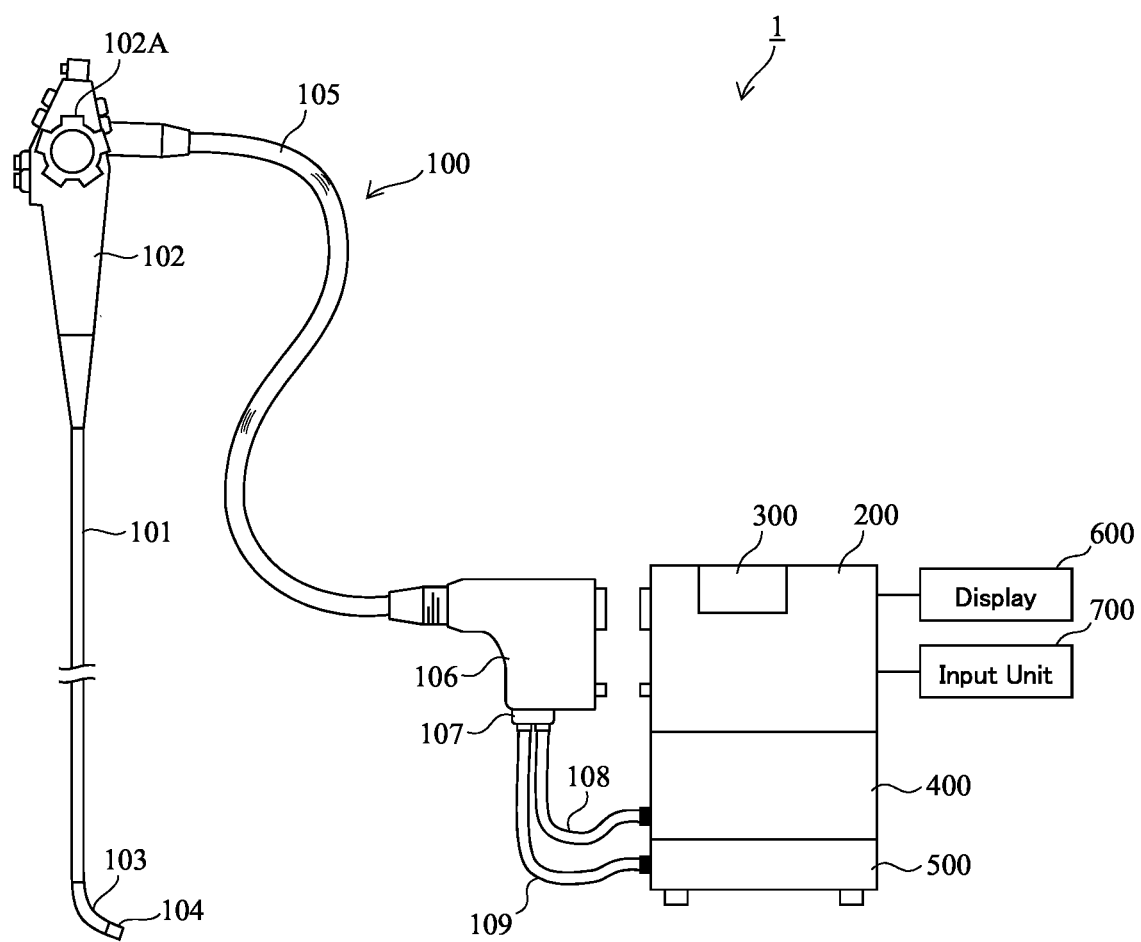
FIG. 1 is an external perspective view of an endoscope system 1 according to a first embodiment of the present invention.
Figure 2:
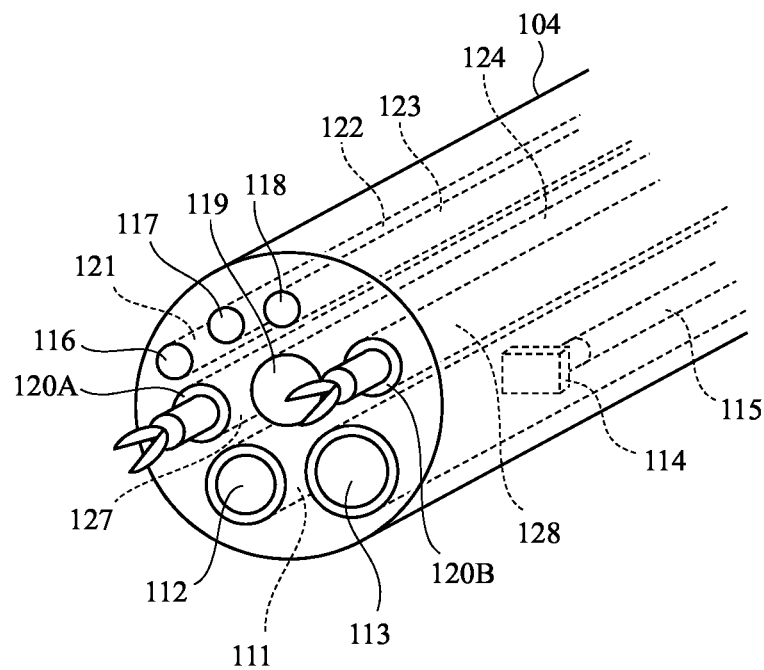
FIG. 2 is a perspective view describing an internal structure of a distal end portion of an endoscope 100.

First, an endoscope system according to an embodiment of the present invention will be described in detail. FIG. 1 is an external perspective view of an endoscope system 1 according to the first embodiment. FIG. 2 is a perspective view describing an internal structure of a distal end portion of an endoscope 100. The endoscope system 1 is primarily configured of the endoscope 100, a processor 200, a light source device 300, a water supply/air supply unit 400, a suction unit 500, a display 600, and an input unit 700.

The endoscope 100 is configured to be insertable into a body of a subject and has a function of capturing an image of a photographic subject and transmitting an image signal of the captured image to the processor 200. The processor 200 receives the image signal from the endoscope 100 and performs predetermined signal processing.

The light source device 300 is configured to be couplable to the processor 200 and internally includes a light source unit that emits irradiated light with which the photographic subject is irradiated. The subject is irradiated with the light from the light source unit via a light guide described later. The light source device 300 may be configured to be separated from the processor 200 and configured to be couplable to the processor 200, or may be embedded into the processor 200.

The water supply/air supply unit 400 includes an air pump and a water flow pump (not illustrated) to discharge a water flow or an airflow supplied to the subject. The suction unit 500 includes a pump and a tank (not illustrated) to suction a bodily fluid and a resected substance suctioned from the inside of the body of the subject via an insertion portion 101.

The display 600 is a display device to perform display based on, for example, a data processing result by the processor 200. The input unit 700 is a device to input commands from an operator in various kinds of measurement operations.

The endoscope 100 includes the insertion portion 101, a hand operating unit 102, a bending portion 103, a distal end portion 104, a universal cable 105, and a connector 106.

As illustrated in FIG. 1, the endoscope 100 has flexibility and includes the insertion portion 101 to be inserted into the body of the subject. The insertion portion 101 has one end coupled to the hand operating unit 102. Besides, the hand operating unit 102 includes, for example, a bending operation knob 102A and an operation unit operable by a user. The hand operating unit 102 is a part to cause the operator to perform various types of operations for capturing an image by the endoscope system 1.

The bending portion 103 configured to be bent is disposed at the distal end of the insertion portion 101. Pulling an operation wire (not illustrated) in conjunction with a rotating operation of the bending operation knob 102A disposed on the hand operating unit 102 bends the bending portion 103. Further, the distal end portion 104 that includes an imaging device (an imaging unit) is joined to the distal end of the bending portion 103. The direction of the distal end portion 104 changes according to the bending operation of the bending portion 103 by the rotating operation of the bending operation knob 102A, thus ensuring the changed photographed area by the endoscope 100. The universal cable 105 extends from the opposite side of the hand operating unit 102 to the connector 106. Similarly to the insertion portion 101, the universal cable 105 internally includes a light guide, various types of wirings, and various types of conduits.

The connector 106 includes various types of connectors for coupling the endoscope 100 to the processor 200. The connector 106 includes a water supply/air supply tube 108 as a passage to transmit a water flow and an airflow from the water supply/air supply unit 400 to the insertion portion 101 and a suction tube 109 to introduce the bodily fluid and the resected substance suctioned from the inside of the body of the subject to the suction unit 500.

With reference to FIG. 2, the internal structure of the endoscope 100 will be described. FIG. 2 is a perspective view illustrating an enlarged structure of the part of the distal end portion 104 in the endoscope 100.

A light guide 111 extends across inside of the endoscope 100 from the distal end portion 104 to the connector 106. The light from the light source unit of the light source device 300 is guided by the light guide 111, condensed by a condenser lens 112 disposed at the distal end, and the subject is irradiated with the light.

The endoscope 100 includes an objective lens 113 and an imaging device 114 in the distal end portion 104. The objective lens 113 condenses scattered light and reflected light from the subject to form an image of the subject on a photo-receiving surface of the imaging device 114.

As one example, the imaging device 114 can be constituted of a Complimentary Metal Oxide Semiconductor Sensor (a CMOS sensor). The imaging device 114 is controlled by a signal (such as a gain control signal, an exposure control signal, and a shutter speed control signal) supplied from the processor 200 via an electrical wiring 115 and supplies an image signal of the captured image to the processor 200 via the electrical wiring 115 and an A/D converter circuit (not illustrated).

A water supply port 116, an air supply port 117, an auxiliary water supply port 118, and a suction port 119 are disposed as end portions or openings of the various types of conduits in the end surface of the distal end portion 104 of the endoscope 100. The water supply port 116 is coupled to the water supply conduit 121 to introduce the water flow for, for example, cleaning the distal end portion 104 from the water supply/air supply unit 400. Additionally, the air supply port 117 is coupled to the air supply conduit 122 to introduce the airflow from the water supply/air supply unit 400. The auxiliary water supply port 118 is coupled to the auxiliary water supply conduit 123 to introduce auxiliary supply water, such as a cleaning fluid and a staining fluid to remove excrement within the visual field, from the water supply/air supply unit 400. Further, the suction port 119 is coupled to the suction conduit 124 to introduce the bodily fluid and the resected substance suctioned from the inside of the body of the subject to the suction unit 500. The conduits 121 to 124 are disposed so as to extend along inside the distal end portion 104, the bending portion 103, the insertion portion 101, the hand operating unit 102, and the universal cable 105.

In addition to the conduits 121 to 124, the endoscope 100 internally includes treatment instrument conduits 127 and 128. Treatment instruments, such as forceps, are disposed inside the treatment instrument conduits 127 and 128 to freely advance and retreat. Distal ends of the treatment instrument conduits 127 and 128 constitute treatment instrument openings 120A and 120B in the distal end portion 104.

The above-described conduits 121 to 124 are divided at the proximity of the coupling portion between the hand operating unit 102 and the insertion portion 101, and the conduits before and after the division are relayed (coupled) with a relay portion (a first relay portion 201 and a second relay portion 202). In this embodiment, for ease of the coupling work with the relay portion, the configuration described below is provided.

Figure 3:
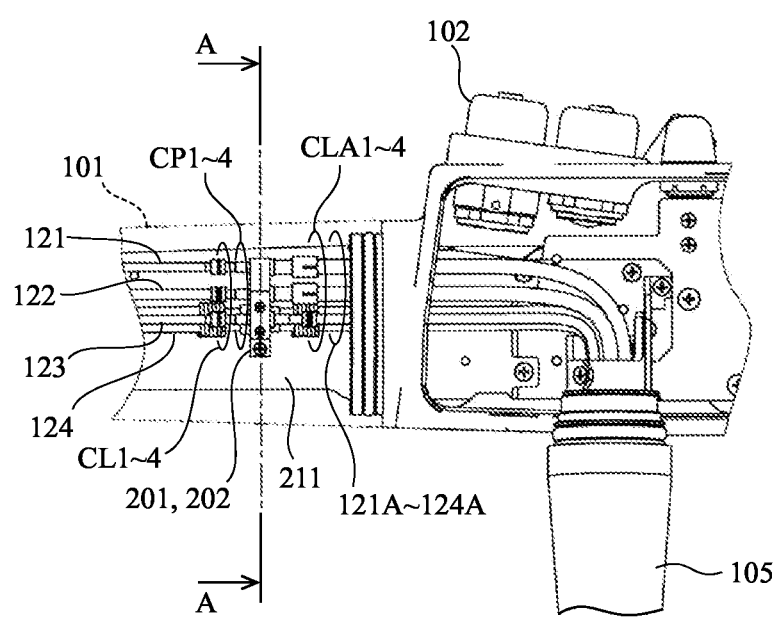
FIG. 3 is a plan view describing a structure of relay portions of conduits 121 to 124.
Figure 4:
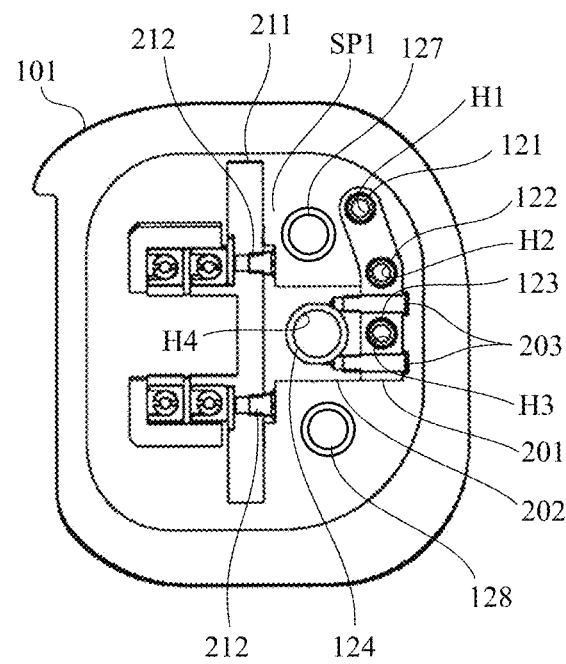
FIG. 4 is a cross-sectional view describing the structure of the relay portions of the conduits 121 to 124.
Figure 5:
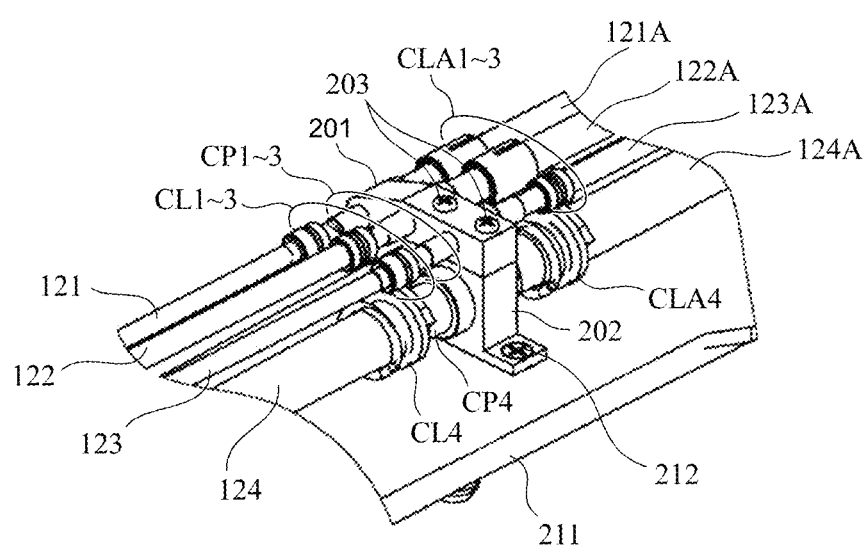
FIG. 5 is a perspective view describing the structure of the relay portion of the conduits 121 to 124.

With reference to FIG. 3 to FIG. 5, the structure of the relay portion of the conduits 121 to 124 will be described. FIG. 3 is a plan view at the proximity of the relay portions. FIG. 4 is a cross-sectional view taken along A-A in FIG. 3. FIG. 5 is a perspective view at the proximity of the relay portion.

As illustrated in FIG. 3, the water supply conduit 121, the air supply conduit 122, the auxiliary water supply conduit 123, and the suction conduit 124 extend, inside the insertion portion 101, along the longitudinal direction of the insertion portion 101. Meanwhile, a water supply conduit 121A, an air supply conduit 122A, an auxiliary water supply conduit 123A, and a suction conduit 124A extend inside the universal cable 105 and the hand operating unit 102. The water supply conduit 121, the air supply conduit 122, the auxiliary water supply conduit 123, and the suction conduit 124 are relayed with (coupled to) the water supply conduit 121A, the air supply conduit 122A, the auxiliary water supply conduit 123A, and the suction conduit 124A at the first relay portion 201 and the second relay portion 202.

The hand operating unit 102 has a base plate 211 as a fixing member. The base plate 211 is a plate-shaped member fixed to a housing of the hand operating unit 102 and extends to the side of the insertion portion 101. The above-described first relay portion 201 and second relay portion 202 are fixedly mounted on the base plate 211.

With reference to FIG. 4, the structure of the relay portion (the first relay portion 201 and the second relay portion 202) will be described. The relay portion illustrated in the drawing includes the first relay portion 201 and the second relay portion 202. Both of the first relay portion 201 and the second relay portion 202 are configured to be directly or indirectly mountable on the base plate 211.

In the example of FIG. 4, the second relay portion 202 has a structure fixable to the base plate 211 with screws 212. Meanwhile, the first relay portion 201 has a structure fixable to the second relay portion 202 with screws 203. In view of this, the first relay portion 201 and the second relay portion 202 are fixedly disposed to the base plate 211. However, the structure illustrated in the drawing is merely an example, and as long as the relay portions can be fixedly disposed to the base plate 211, any fixation method is available. For example, a structure in which each of the first relay portion 201 and the second relay portion 202 is directly fixed to the base plate 211 can be employed. Additionally, the vertical relationship between the first relay portion 201 and the second relay portion 202 can be made opposite. The number of the relay portions is not limited to two, and can be three or more.

The base plate 211 is one example of the fixing member to fix the first relay portion 201 and the second relay portion 202, and the fixing member is not limited to this. The first relay portion 201 and the second relay portion 202 only need to be couplable to the fixing member that is immovable with respect to the hand operating unit 102, and details of the method is not particularly limited.

As illustrated in FIG. 3 and FIG. 5, the first relay portion 201 couples to the water supply conduit 121, the air supply conduit 122, and the auxiliary water supply conduit 123 at one side thereof and couples the water supply conduit 121A, the air supply conduit 122A, and the auxiliary water supply conduit 123A at the other side thereof. As illustrated in FIG. 4, the first relay portion 201 has hole portions H1 to H3 that penetrate from the front surface to the back surface, and relay pipes CP1 to CP3 for relay are insertable into and fixable to these hole portions H1 to H3. The relay pipes CP1 to CP3 extend from one side to the other side of the first relay portion 201. The conduits 121 to 123 are fixed to one ends of the relay pipes CP1 to CP3 with pipe stoppers CL1 to CL3. The conduits 121A to 123A are fixed to the other ends of the relay pipes CP1 to CP3 with pipe stoppers CLA1 to CLA3.

As illustrated in FIG. 3 and FIG. 5, the second relay portion 202 couples to the suction conduit 124 at one side thereof and couples to the suction conduit 124A at the other side thereof. As illustrated in FIG. 4, the second relay portion 202 has a hole portion H4 that penetrates from the front surface to the back surface, and a relay pipe CP4 for relay is insertable into and fixable to this hole portion H4. The suction conduit 124 is fixed to one end of this relay pipe CP4 with a pipe stopper CL4. The suction conduit 124A is fixed to the other end of the relay pipe CP4 with a pipe stopper CLA4.

In the example illustrated in FIG. 3 to FIG. 5, the first relay portion 201 has the shape of disposing the hole portions H1 to H3 along the direction approximately parallel to the plate surface of the base plate 211, but this shape is an example and the shape is not limited to this. In the example illustrated in FIG. 3 to FIG. 5, a width in the lateral direction (a direction intersecting with the longitudinal direction of the insertion portion 101) of the first relay portion 201 is larger than a width in the lateral direction of the second relay portion 202. Thus, a space SP1 is formed between the first relay portion 201 and the base plate 211, and, for example, the treatment instrument conduit 127 can be disposed in this space SP1. The treatment instrument conduit 127 is sandwiched between the first relay portion 201 and the base plate 211 in the space SP1. This allows stably disposing the treatment instrument conduit 127 in the insertion portion 101, thereby ensuring the efficient assembly work.

Figure 6A:
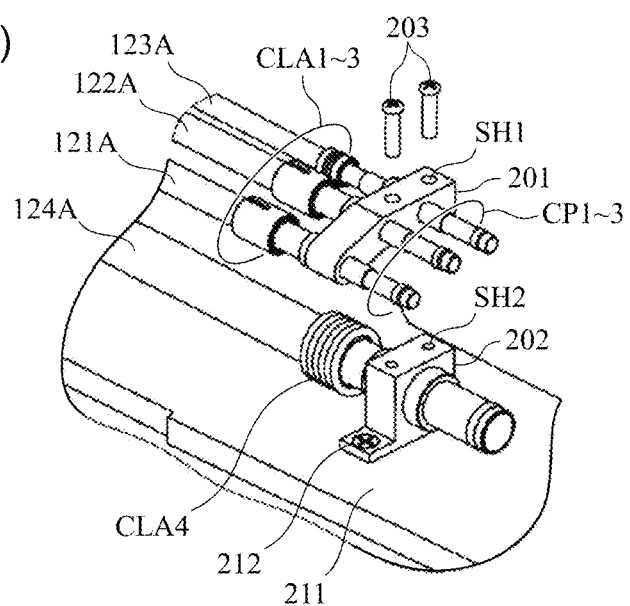
FIGS. 6(a) and 6(b) are perspective views describing a procedure for assembly of the relay portion.
Figure 6B:
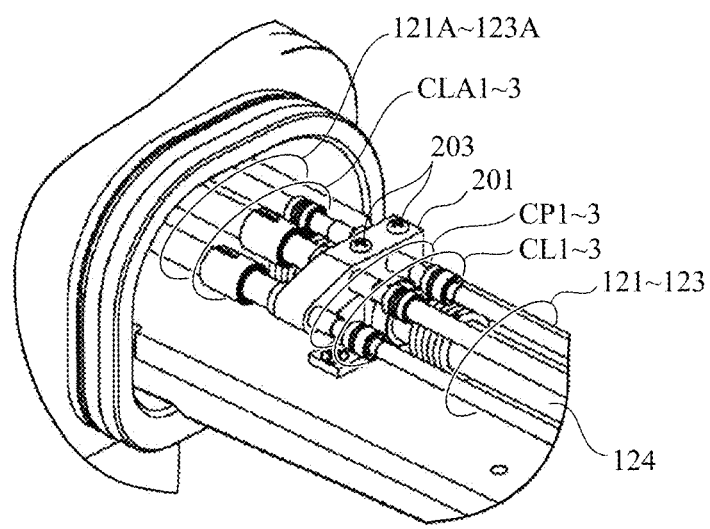
Figure 7A:
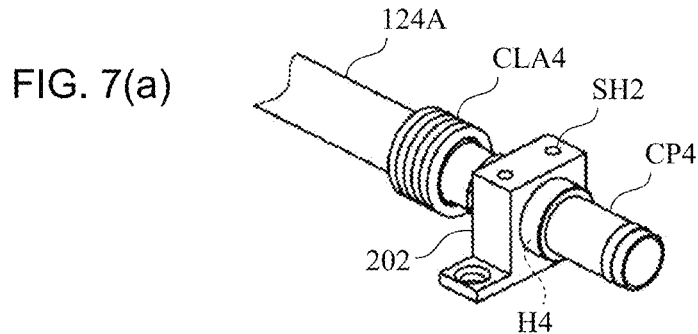
FIGS. 7(a) and 7(b) are perspective views describing a procedure for the assembly of the relay portion.
Figure 7B:
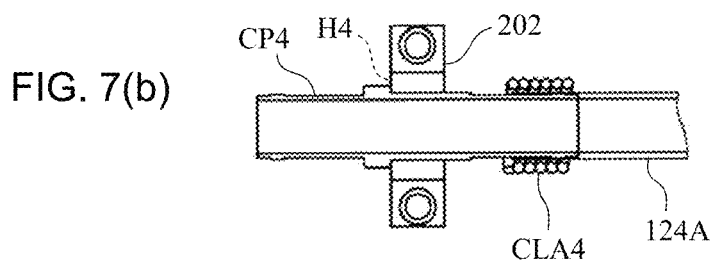
Figure 8A:
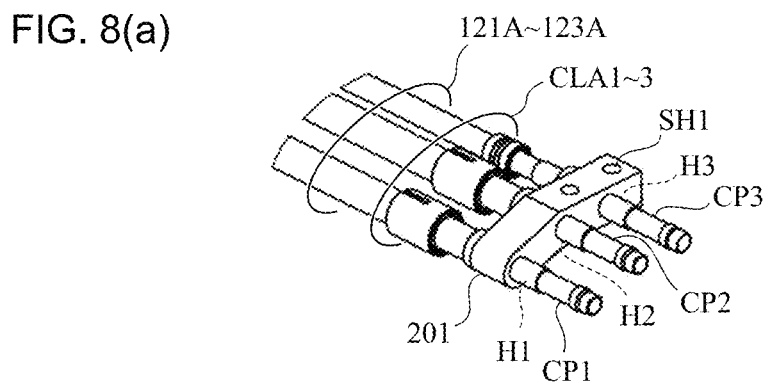
FIGS. 8(a) and 8(b) are perspective views describing the procedure for the assembly of the relay portion.
Figure 8B:
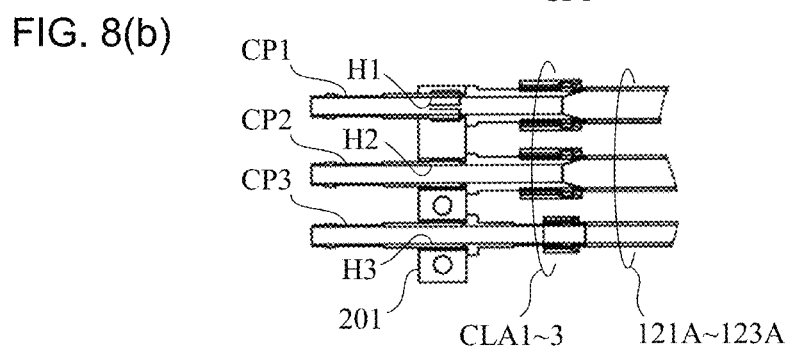

With reference to FIG. 6 to FIG. 8, a procedure for the assembly of the first relay portion 201 and the second relay portion 202 will be described. As illustrated in FIG. 6, in this embodiment, the second relay portion 202 is fixed to the base plate 211 with the screws 212, and the first relay portion 201 is fixed to the second relay portion 202 with the screws 203.

Before the second relay portion 202 is fixed to the base plate 211 by fastening the screws, as illustrated in FIG. 7, the relay pipe CP4 is inserted into and fixed to the hole portion H4, and the conduit 124A is coupled to the other end side of the relay pipe CP4 via the pipe stopper CLA4. Afterwards, the second relay portion 202 is fixed with the screws 212.

Similarly, before the first relay portion 201 is fixed to the second relay portion 202 by fastening the screws, as illustrated in FIG. 8, the relay pipes CP1 to 3 are inserted into and fixed to the hole portions H1 to H3, and the conduits 121A to 123A are coupled to the other end sides of the relay pipes CP1 to 3 via the pipe stoppers CLA1 to 3.

Afterwards, in the first relay portion 201, the screws 203 are inserted into screw holes SH1, and the screws 203 are screwed into screw holes SH2 in the second relay portion 202 (see (a) in FIG. 6). Subsequently, conduits 121 to 123 are coupled to one ends of the relay pipes CP1 to 3 via the pipe stoppers CL1 to CL3. At this time, since the first relay portion 201 and the second relay portion 202 have already been fixed to the base plate 211, a worker can perform the assembly work by holding the pipe stoppers CL1 to 4 and the conduits 121 to 124 alone.

As described above, according to the endoscope of this embodiment, the relay portions to couple the conduits have the structure in which the relay portions are fixable to the fixing member fixed to the hand operating unit 102. Therefore, the coupling work of the conduits can be performed on the fixedly disposed relay portions. In view of this, the efficiency of the assembly work of the conduits can be improved. Additionally, application of an excessive force to the conduits during the work is suppressed, thereby ensuring the reduced risk of causing damage, such as buckling, of the conduit. Further, even during the maintenance, the work can be performed while fixing the conduits as the coupling targets with the relay portions 201 and 202, and therefore ensuring the efficient maintenance work.

Second Embodiment

Figure 9A:
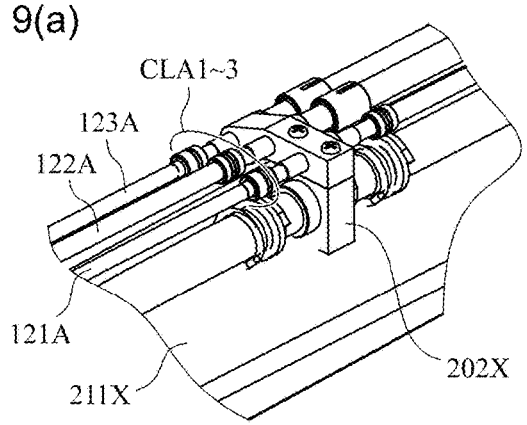
FIGS. 9(a) through 9(d) are perspective views describing a configuration of the endoscope system 1 according to a second embodiment of the present invention.
Figure 9C:
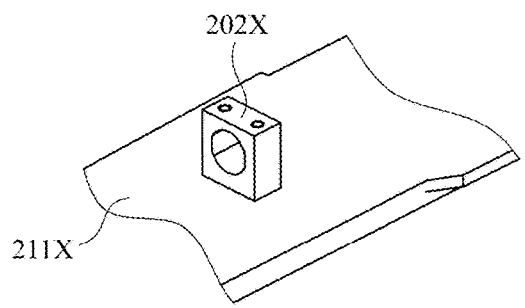
Figure 9B:
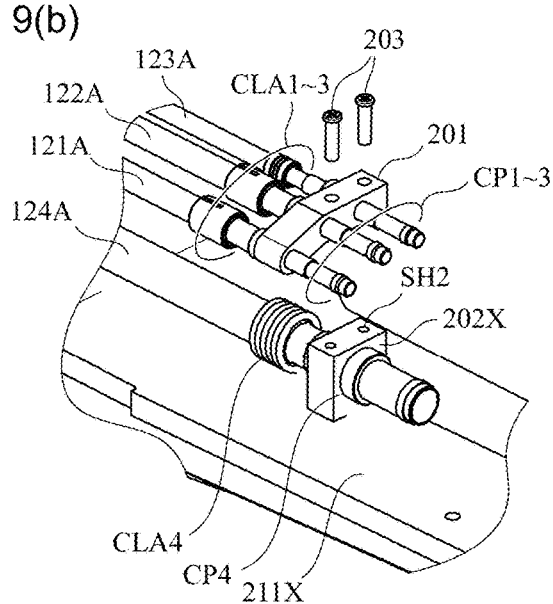
Figure 9D:
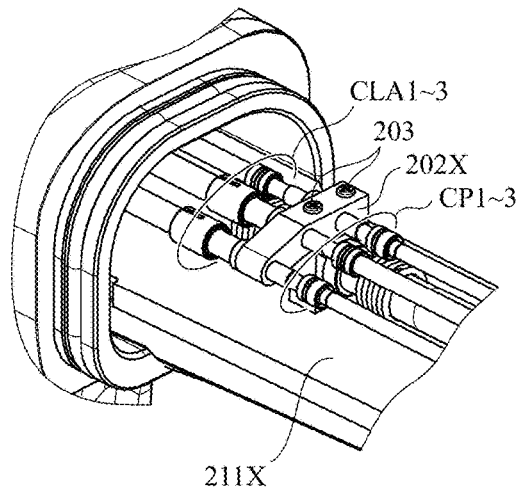

Next, the endoscope system 1 according to the second embodiment of the present invention will be described with reference to FIG. 9. Since the whole structure of the endoscope system 1 of the second embodiment is similar to that of the first embodiment (FIG. 1 and FIG. 2), the overlapping description will be omitted below. The second embodiment differs from the first embodiment in details of a configuration of relay portions. FIG. 9(a) is a perspective view when the proximity of the relay portions is viewed from the pipe stoppers CLA1 to 3 side, and FIG. 9(b) is a perspective view when the proximity of the relay portions is viewed from the relay pipes CP1 to CP3 side. FIG. 9(c) is a perspective view of a second relay portion 202X, and FIG. 9(d) is a perspective view illustrating a state after assembly of the relay portions.

In this second embodiment, as illustrated in FIG. 9(c), the second relay portion 202X is configured integrally with a base plate 211X, which is different from the first embodiment. As illustrated in FIG. 9(b), in the assembly of the endoscope system 1 of this second embodiment, the relay pipe CP4 is inserted into and fix to the second relay portion 202X integrated with the base plate 211X, and the conduit 124A is coupled to the other end side of the relay pipe CP4 via the pipe stopper CLA4. Similarly to the first embodiment, before the first relay portion 201 is fixed to the second relay portion 202X by fastening the screws, the relay pipes CP1 to 3 are inserted into and fixed to the hole portions H1 to H3, and the conduits 121A to 123A are coupled to the other end sides of the relay pipes CP1 to 3 via the pipe stoppers CLA1 to 3.

Subsequently, inserting the screws 203 into the screw holes SH1 and screwing the screws 203 into the screw holes SH2 in the second relay portion 202 fixes the first relay portion 201 to the second relay portion 202X. Thereafter, as illustrated in FIG. 9(d), the conduits 121 to 124 are coupled to one ends of the relay pipes CP1 to 4 via the pipe stoppers CLA1 to CLA4. At this time, since the first relay portion 201 has already been fixed to the base plate 211 via the second relay portion 202X, the worker can perform the assembly work by holding the pipe stoppers CLA1 to 4 and the conduits 121 to 124 alone.

As described above, with the second embodiment, the effects similar to those of the first embodiment can be obtained. Since the second relay portion 202X is configured integrally with the base plate 211X in the second embodiment, the number of assembly steps can be reduced compared with that of the first embodiment.

Third Embodiment

Figure 10A:
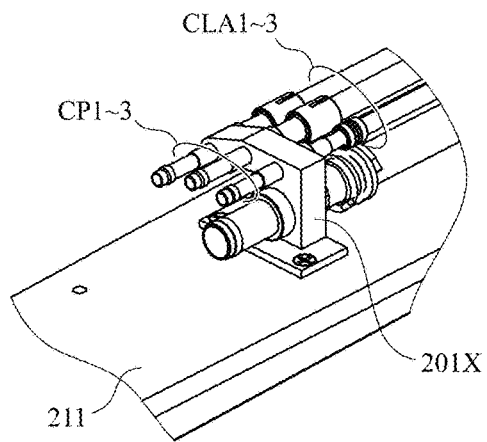
FIGS. 10(a) through 10(d) are perspective views describing a configuration of the endoscope system 1 according to a third embodiment of the present invention.
Figure 10B:
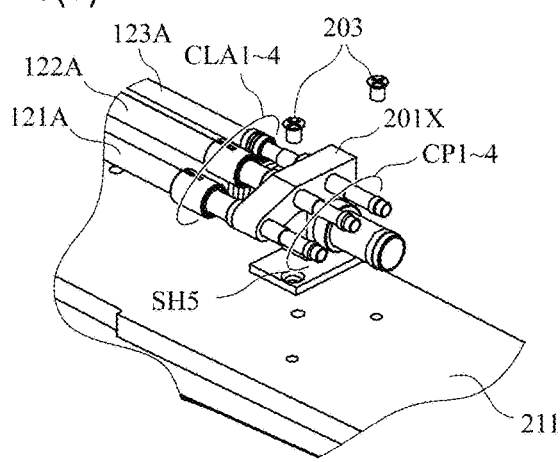
Figure 10C:
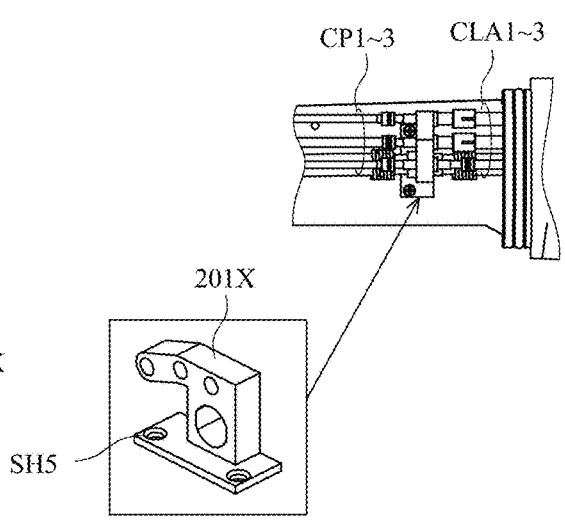
Figure 10D:
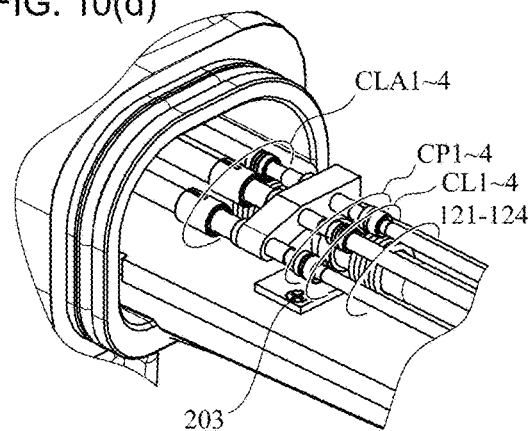

Next, the endoscope system 1 according to the third embodiment of the present invention will be described with reference to FIG. 10. Since the whole structure of the endoscope system 1 of the third embodiment is similar to that of the first embodiment (FIG. 1 and FIG. 2), the overlapping description will be omitted below. The third embodiment differs from the first embodiment in details of a configuration of relay portion. FIG. 10(a) is a perspective view when the proximity of the relay portion is viewed from the pipe stoppers CLA1 to 3 side, and FIG. 10(b) is a perspective view when the proximity of the relay portion is viewed from the relay pipes CP1 to CP3 side. FIG. 10(c) is a perspective view of a relay portion 201X, and FIG. 10(d) is a perspective view illustrating a state after assembly of the relay portion.

In this third embodiment, as illustrated in FIG. 10(b), the relay portion 201X is directly fastened with screws to be fixable to the base plate 211. In other words, the relay portion 201X has a shape in which the first relay portion 201 and the second relay portion 202 of the first embodiment are integrally configured.

As illustrated in FIG. 10(b), in the assembly of the endoscope system 1 of this third embodiment, the relay pipes CP1 to 4 are inserted into and fix to the relay portion 201X, and the conduits 121A to 124A are coupled to the other end sides of the relay pipes CP1 to 4 via the pipe stoppers CLA1 to 4. Afterwards, inserting the screws 203 into screw holes SH5 fixes the relay portion 201X to the base plate 211. Thereafter, as illustrated in FIG. 10(d), the conduits 121 to 124 are coupled to one ends of the relay pipes CP1 to 4 via the pipe stoppers CL1 to CL4.

As described above, with the third embodiment, the effects similar to those of the first embodiment can be obtained. Since the number of the relay portions is reduced in the third embodiment, the number of assembly steps can be reduced by the amount compared with those of the above-described embodiments.

Fourth Embodiment

Figure 11A:
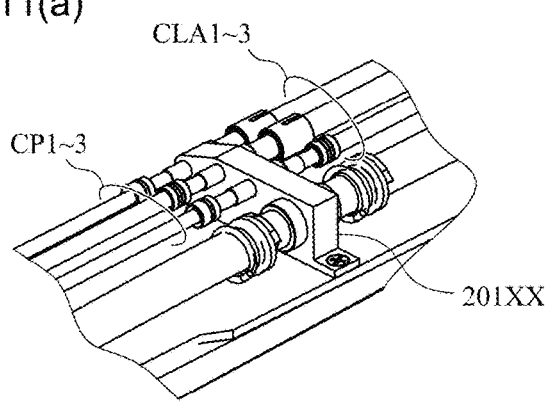
FIGS. 11(a) through 11(d) are perspective views describing a configuration of the endoscope system 1 according to a fourth embodiment of the present invention.
Figure 11C:
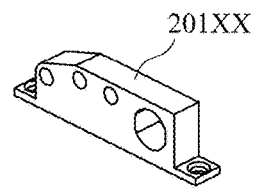
Figure 11B:
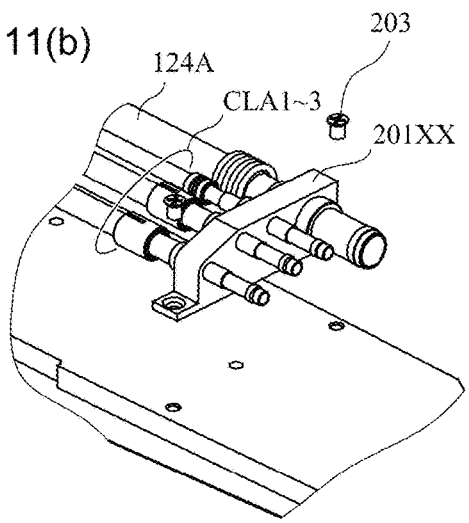
Figure 11D:
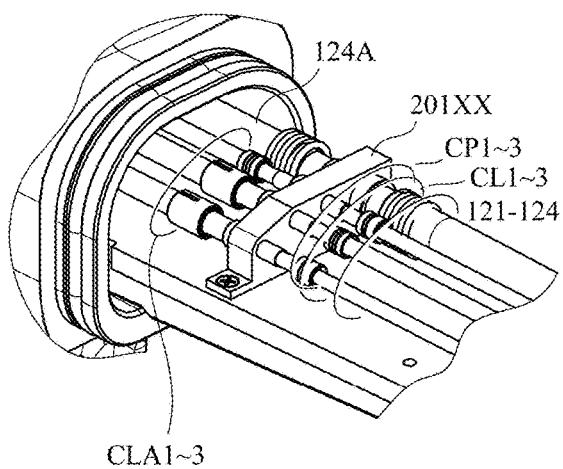

Next, the endoscope system 1 according to the fourth embodiment of the present invention will be described with reference to FIG. 11. Since the whole structure of the endoscope system 1 of the fourth embodiment is similar to that of the first embodiment (FIG. 1 and FIG. 2), the overlapping description will be omitted below. The fourth embodiment differs from the first embodiment in details of a configuration of a relay portion. FIG. 11(a) is a perspective view when the proximity of the relay portion is viewed from the pipe stoppers CLA1 to 3 side, and FIG. 11(b) is a perspective view when the proximity of the relay portions is viewed from the relay pipes CP1 to CP3 side. FIG. 11(c) is a perspective view of a relay portion 201XX, and FIG. 11(d) is a perspective view illustrating a state after assembly of the relay portion.

In this fourth embodiment, as illustrated in FIG. 11(b), similarly to the relay portion 201X of the third embodiment, the relay portion 201XX is directly fastened with screws to be fixable to the base plate 211. In other words, the relay portion 201XX has a shape in which the first relay portion 201 and the second relay portion 202 of the first embodiment are integrally configured. However, in this relay portion 201XX, insertion holes of the relay pipes CP1 to 4 are arranged parallel to the base plate 211. Other than that, the fourth embodiment is similar to the third embodiment.

Others

The present invention is not limited to the above-described embodiments, and includes various modifications. For example, the above-described embodiments are described in detail for ease of understanding of the present invention, and does not necessarily include all of the described configurations. A part of the configuration of one embodiment can be replaced by the configuration of another embodiment. The configuration of another embodiment can be added to the configuration of one embodiment. Addition, deletion, or replacement of another configuration can be performed on a part of the configuration in each of the embodiments.

REFERENCE SIGNS LIST

1 Endoscope system
100 Endoscope
101 Insertion portion
102 Hand operating unit
102A Bending operation knob
103 Bending portion
104 Distal end portion
105 Universal cable
106 Connector
108 Water supply/air supply tube
109 Suction tube
111 Light guide
112 Condenser lens
113 Objective lens
114 Imaging device
115 Electrical wiring
116 Water supply port
117 Air supply port
118 Auxiliary water supply port
119 Suction port
120A, 120B Treatment instrument opening
121 Water supply conduit
121A Water supply conduit
122 Air supply conduit
122A Air supply conduit
123 Auxiliary water supply conduit
123A Auxiliary water supply conduit
124 Suction conduit
124A Suction conduit
127 Treatment instrument conduit
128 Treatment instrument conduit
200 Processor
201 First relay portion
202, 202X Second relay portion
201X, 201XX Relay portion
203 Screw
211 Base plate
212 Screw
300 Light source device
400 Water supply/air supply unit
500 Suction unit
600 Display
700 Input unit
CP1 to 4 Relay pipe
H1 to 4 Hole portion
SP1 Space

The invention claimed is:

1. An endoscope comprising:
an insertion portion;
a hand operating unit coupled to the insertion portion;
a plurality of conduits disposed inside the insertion portion and the hand operating unit;
a base fixedly disposed to the hand operating unit; and
a relay disposed proximally to the plurality of conduits and which relays the plurality of conduits, the relay comprising:
a first relay portion that relays a first conduit among the plurality of conduits, the first relay portion having a space between the base and the first relay portion; and
a second relay portion that relays a second conduit among the plurality of conduits, wherein:
the first relay portion is fixable to the second relay portion,
the second relay portion is fixable to the base such that the second relay portion is sandwiched between the first relay portion and the base in a direction orthogonal to a direction of the insertion portion, and
the first relay portion has a width in a second direction intersecting with a first direction as a longitudinal direction of the insertion portion, the width being larger than a width of the second relay portion in the second direction.

2. The endoscope according to claim 1, wherein the base is a plate-shaped member that extends from the hand operating unit in a direction of the insertion portion.

3. The endoscope according to claim 1, wherein the relay includes a relay pipe that extends from a first surface to a second surface thereof, and
wherein the relay pipe has one end to which a conduit of the plurality of conduits at a first side is coupled, and the relay pipe has another end to which the conduit of the plurality of conduits at a second side is coupled.

* * * * *